United States Patent [19]

Smith et al.

[11] 4,326,090

[45] Apr. 20, 1982

[54] DESTRUCTION OF PCB'S

[75] Inventors: James G. Smith; Gurbachan L. Bubbar, both of Waterloo, Canada

[73] Assignee: University of Waterloo, Waterloo, Canada

[21] Appl. No.: 194,972

[22] Filed: Oct. 8, 1980

[51] Int. Cl.$^3$ .......................... C07C 1/20; C02F 1/70

[52] U.S. Cl. .................................. 585/469; 210/757; 570/204

[58] Field of Search ........................ 585/469; 570/204; 210/757

[56] References Cited

U.S. PATENT DOCUMENTS 4,284,516 8/1981 Parker et al. ....................... 585/469

OTHER PUBLICATIONS

"Electronic Engineering Times", Oct. 29, 1979, pp. 1 and 4.

Oku et al., *Chemistry & Industry,* Nov. 4, 1978, pp. 841-842.

Behr, "The Washington Post", Aug. 22, 1980, p. E1.

*Primary Examiner*—Curtis R. Davis
*Attorney, Agent, or Firm*—Sim & McBurney

[57] ABSTRACT

Polychlorinated biphenyls (PCB's) are dechlorinated and rendered environmentally harmless by reaction with preformed sodium naphthalenide in a suitable ether-type solvent. The reaction proceeds rapidly at ambient temperature and effects substantially complete removal of chlorine from the PCB's.

10 Claims, 1 Drawing Figure

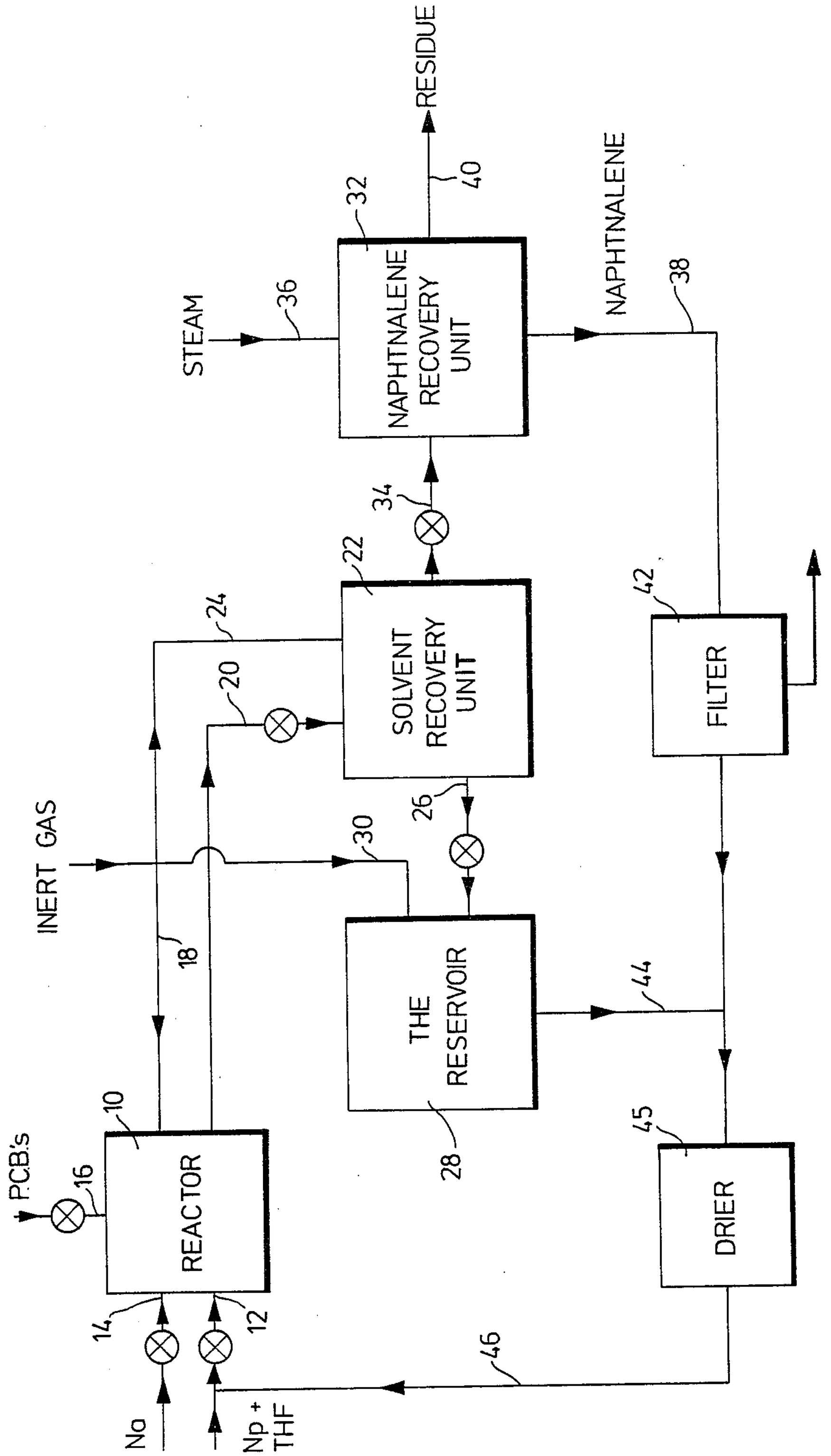
RESIDUE
40
32
NAPHTNALENE
STEAM
36
NAPHTNALENE RECOVERY UNIT
38
34
22
42
24
SOLVENT RECOVERY UNIT
FILTER
20
INERT GAS
26
30
18
THE RESERVOIR
44
10
28
45
P.C.B.'s
16
REACTOR
DRIER
14
12
46
Na
Np + THF

DESTRUCTION OF PCB'S

FIELD OF INVENTION

The present invention relates to the conversion polychlorinated biphenyls (PCB's) to essentially chlorine-free environmentally-safe material.

BACKGROUND TO THE INVENTION

Polychlorinated biphenyls are extremely useful materials and are widely used as insulators and in heat exchangers. However, they are also almost indestructible by the environment and when present in water bodies concentrate in the tissue of fish, and can have an adverse effect on humans eating the fish.

Procedures to dispose of PCB's have been sought and the only procedure which has been practised to any degree is to burn the PCB's at high temperature. This procedure is unsatisfactory since potentially toxic gases are produced, complete combustion must be effected to prevent PCB escape and destruction of otherwise potentially-valuable material associated with the PCB's also occurs.

SUMMARY OF INVENTION

In accordance with the present invention, there is provided a method of converting PCB's to environmentally-acceptable dechlorinated material.

While the process of the invention is described hereinafter with particular reference to the dechlorination of polychlorinated biphenyls, the process of the invention may be applied to the halogenation of any polyhalogenated organic material, for example, DDT. The present invention involves reacting polychlorinated biphenyls with sodium naphthalenide.

BRIEF DESCRIPTION OF DRAWING

The sole FIGURE of the drawing is a schematic flow sheet of one embodiment of the invention.

GENERAL DESCRIPTION OF INVENTION

The present invention involves the reaction of sodium naphthalenide with polychlorinated biphenyl. There is a chemical reaction between the sodium and the organically-bound chlorine to form sodium chloride. The reaction occurs rapidly at ambient temperature in essentially quantitative yield.

The reaction is conveniently effected in an ether-type solvent for both the sodium naphthalenide and the PCB's and under an inert atmosphere. One suitable ether-type solvent is tetrahydrofuran. It is preferred to preform the sodium naphthalenide by reaction of excess sodium with naphthalene in the solvent and then add the PCB's to the sodium naphthalenide solution. The excess of sodium metal usually is at least about 50 mol. %, preferably about 100 to 300 mol. %, based on the naphthalene.

It has been found that the procedure of preformation of sodium naphthalenide followed by reaction of that material with the PCB's is much more efficient in terms of completeness of reaction and length of reaction time than a procedure in which sodium is added to a solution of naphthalene and PCB's in a solvent. In addition, the presence of free sodium metal in the reaction medium, resulting from the use of an excess of sodium metal in the sodium naphthalenide formation, appears to enhance the effectiveness of the dechlorination reaction.

The proportion of sodium naphthalenide used depends on the concentration of chlorine in the PCB's. Theoretically, one atom of sodium in the form of sodium naphthalenide is required for each atom of chlorine in the PCB's. However, in the presence of excess sodium it has been found that a concentration of sodium naphthalenide of about 0.5 of theoretical is satisfactory.

The inert atmosphere in which the reaction is effected may be provided by any convenient inert gas, such as, nitrogen or argon. The reaction between the sodium naphthalenide and the PCB's proceeds rapidly at ambient temperatures (20° to 25° C.), although elevated temperatures may be used, if desired, the reaction being complete in about 30 to 60 minutes.

The process of the invention may be incorporated into a multistep procedure which permits efficient dechlorination of PCB's and recovery of solvent and naphthalene for reuse. In the multistep process, the following operations are effected:

(a) sodium naphthalenide is prepared by reacting naphthalene with an excess of sodium of at least 50 mol. % at ambient temperature (about 20° to 25° C.) in a suitable ether-type solvent, preferably tetrahydrofuran, under an inert atmosphere in a first reaction vessel;

(b) PCB's are dechlorinated by feeding the fluid contaminated by the same or the PCB's themselves into the first reaction vessel to provide a concentration of sodium naphthalenide of about 0.5 to about 1.0 of the theoretical concentration required to remove all the chlorine from the PCB's as sodium chloride, so that reaction between the sodium naphthalenide and the PCB's occurs under an inert atmosphere, resulting in the formation of sodium chloride and substantially dechlorinated polymeric material. The reaction medium may be agitated, if desired, to decrease the reaction time;

(c) the liquid reaction products formed in the first reaction vessels are forwarded to a second reaction vessel wherein the solvent is stripped from the reaction products, leaving metallic sodium remaining in the first vessel for reaction with further naphthalene on the next cycle. The solvent may be essentially completely removed or, preferably, is partially removed so as to leave sufficient residue to maintain the same mobile for removal from the reaction vessel. The stripped solvent is condensed and recycled to the first reaction vessel;

(d) the residual material in the second reaction vessel is removed and forwarded to a naphthalene recovery unit, wherein naphthalene is separated from the residue and recycled to the first reaction vessel. Naphthalene recovery may be effected by a variety of procedures. The first such procedure involves simple sublimation of the naphthalene from the residue. Another such procedure uses steam stripping of the naphthalene from the non-volatile dechlorinated organic material followed by filtration of the naphthalene from the steam distillate. Vacuum distillation of the naphthalene also may be effected.

This multistep process is cyclic in character, whereby a continuous process may be effected with only make-up quantities of naphthalene and solvent being required and with sodium being the major raw material.

Referring to the accompanying drawing, there is shown therein a schematic flow sheet of a PCB dechlorination procedure in accordance with one embodiment of the invention. As shown therein, a dechlorination vessel 10 serves two functions, first as a reaction vessel for naphthalene fed thereto by valved line 12 as a solution in THF with sodium fed thereto by valved line 14, so as to form sodium naphthalenide, and second as a reaction vessel for the sodium naphthalenide and PCB's fed thereto by valved line 16. An inert gas is fed to the dechlorination vessel 10 by line 18 to provide an inert atmosphere for the reactions effected therein and to maintain a small positive pressure therein.

The dechlorinated product is passed by valved line 20 to a solvent recovery vessel 22 wherein solvent is stripped under an inert atmosphere provided by inert gas in line 24. The recovered THF is removed from the vessel 22 by valved line 26 to a THF reservoir 28 from which the THF may be recycled to the dechlorination vessel 10 as described below. An inert atmosphere is provided in the THF reservoir 28 from inert gas in line 30.

Naphthalene-containing residue from the solvent stripping operation is passed from the solvent recovery vessel 22 to a naphthalene recovery vessel 32 by valved line 34. The naphthalene is steam stripped from the residue by steam fed by line 36 and removed by line 38. The solvent- and naphthalene-free residue then is removed by line 40. The naphthalene is separated from the condensed steam by filtration on filter 42 and is recycled, in solution in THF fed by line 44 from the THF reservoir 28, and after drying in drier 45, by line 46 to the naphthalene feed line 12.

The procedure of the present invention, therefore, enables safe disposal of environmentally harmful polychlorinated biphenyls to be effected without the necessity for the use of high temperature combustion procedures. The process of dechlorination occurs rapidly, under mild reaction conditions and is highly efficient. The procedure is capable of continuous operation with recycle of solvent and naphthalene.

EXAMPLES

Example 1

Sodium naphthalenide was prepared by reacting an excess of sodium with 2.0 g of naphthalene in 80 ml of THF at 20° to 25° C. for 2 hours. To this was added 100 g of paraffin oil containing 100 ppm Arochlor 1254 (a polychlorinated biphenyl), so as to simulate a typical PCB-contaminated transformer oil, and the mixture was stirred for 4 hours. A 1% solution of the product in isooctane showed no PCB peaks on gas chromatographic analysis.

Example 2

The effectiveness of two dechlorination procedures was tested. In the first procedure (A), sodium was added to a solution of the PCB compound and naphthalene in the solvent. The second procedure (B) involved reaction of excess sodium with naphthalene to form sodium naphthalenide and then reacting with the PCB in the presence of the excess sodium. In each case the concentration of naphthalene was 1 mole per chlorine atom and the process was carried out at 22° F. in THF solvent.

The results are reproduced in the following Table I:

TABLE I

| Procedure | Arochlor | % Cl Reduction 1016 | 1248 | 1254 |
|---|---|---|---|---|
| A | | 96.7 | — | — |
| B | | 99.3 | 99.4 | 99.8 |

It will be seen from these results that the preforming of the sodium naphthalenide produces superior dechlorination of the PCB's.

Example 3

The procedure of Example 2 was repeated except that DDT was treated in place of the PCB. The results are reproduced in the following Table II:

TABLE II

| Procedure | % Cl Reduction |
|---|---|
| A | 97.8 |
| B | 99.9 |

These results show that DDT may be effectively dechlorinated and that the preformation of sodium naphthalenide produces superior dechlorination of the DDT.

SUMMARY OF DISCLOSURE

In summary of this disclosure, the present invention provides a mild-condition effective method of rendering PCB's and other halogenated organic materials harmless by dechlorinating the same by rapid reaction with sodium naphthalenide. Modifications are possible within the scope of the invention.

What we claim is:

1. A process of dehalogenating a polyhalogenated organic material, which comprises reacting said polyhalogenated organic material with sodium naphthalenide in the presence of sodium metal.

2. The process of claim 1 wherein said polyhalogenated organic material is a polychlorinated biphenyl.

3. The process of claim 2 wherein said sodium naphthalenide is formed by reacting sodium with naphthalene and the latter reaction is complete prior to said reaction with said polychlorinated biphenyl.

4. A process for dechlorinating polychlorinated biphenyls, which comprises:

(a) reacting sodium with naphthalene to form sodium naphthalenide, (b) reacting the sodium naphthalenide so formed with said polychlorinated biphenyls in the presence of sodium metal.

5. The process of claim 4 wherein reaction steps (a) and (b) are effected at a temperature of about 20° to 25° C. under an inert atmosphere in an ether-based solvent for said sodium naphthalenide.

6. The process of claim 5 wherein said solvent is tetrahydrofuran.

7. A cyclic process for the destruction of PCB's, which comprises:

(a) feeding sodium, naphthalene and an ether-type solvent for naphthalene to a reaction zone to cause reaction of the sodium with the naphthalene to form sodium naphthalenide, and leave an excess of at least about 50 mol. % of sodium metal, (b) after completion of step (a), feeding said PCB's to said reaction zone in an amount to provide at least about 0.5 mole of naphthalene per atom of chlorine in said PCB's and to cause reaction of the sodium naphthalenide with said PCB's to effect substantially complete dechlorination of said PCB's and form a liquid product mixture and sodium metal, (c) forwarding said liquid product mixture to a solvent recovery zone physically separate from said reaction zone while leaving said sodium metal in said reaction zone, removing at least a major portion of said solvent from said product mixture in said solvent recovery zone and leaving a solvent-stripped mixture, (d) recovering said removed solvent and recycling the same to said step (a), (e) forwarding said solvent stripped mixture to a naphthalene recovery zone physically separate from both said reaction zone and said solvent recovery zone and removing naphthalene and any residual solvent from said solvent stripped mixture in said naphthalene recovery zone, and (f) recovering said removed naphthalene and residual solvent and recycling the same to said step (a).

8. The process of claim 7 wherein steps (a), (b) and (c) are effected under an inert atmosphere.

9. The process of claim 7 wherein said steps (a) and (b) are effected at a temperature of about 20° to 25° C.

10. The process of claim 7, 8 or 9 wherein said ether-type solvent is tetrahydrofuran.

* * * * *

UNITED STATES PATENT AND TRADEMARK OFFICE

CERTIFICATE OF CORRECTION

PATENT NO. : 4,326,090 Page 1 of 2

DATED : April 20, 1982

INVENTOR(S) : James G. Smith et al.

It is certified that error appears in the above-identified patent and that said Letters Patent is hereby corrected as shown below:

The Title Page should be deleted to appear as per attached Title Page.

Signed and Sealed this

*Thirteenth* Day of *July 1982*

[SEAL]

*Attest:*

GERALD J. MOSSINGHOFF

*Attesting Officer* *Commissioner of Patents and Trademarks*

United States Patent [19]

Smith et al.

[11] 4,326,090

[45] Apr. 20, 1982

[54] DESTRUCTION OF PCB'S

[75] Inventors: James G. Smith; Gurbachan L. Bubbar, both of Waterloo, Canada

[73] Assignee: University of Waterloo, Waterloo, Canada

[21] Appl. No.: 194,972

[22] Filed: Oct. 8, 1980

[51] Int. Cl.[3] .......................... C07C 1/20; C02F 1/70

[52] U.S. Cl. .................................. 585/469; 210/757; 570/204

[58] Field of Search ........................ 585/469; 570/204; 210/757

[56] References Cited

U.S. PATENT DOCUMENTS 4,284,516 8/1981 Parker et al. ...................... 585/469

OTHER PUBLICATIONS

"Electronic Engineering Times", Oct. 29, 1979, pp. 1 and 4.

Oku et al., *Chemistry & Industry*, Nov. 4, 1978, pp. 841–842.

Behr, "The Washington Post", Aug. 22, 1980, p. E1.

*Primary Examiner*—Curtis R. Davis

*Attorney, Agent, or Firm*—Sim & McBurney

[57] ABSTRACT

Polychlorinated biphenyls (PCB's) are dechlorinated and rendered environmentally harmless by reaction with preformed sodium naphthalenide in a suitable ether-type solvent. The reaction proceeds rapidly at ambient temperature and effects substantially complete removal of chlorine from the PCB's.

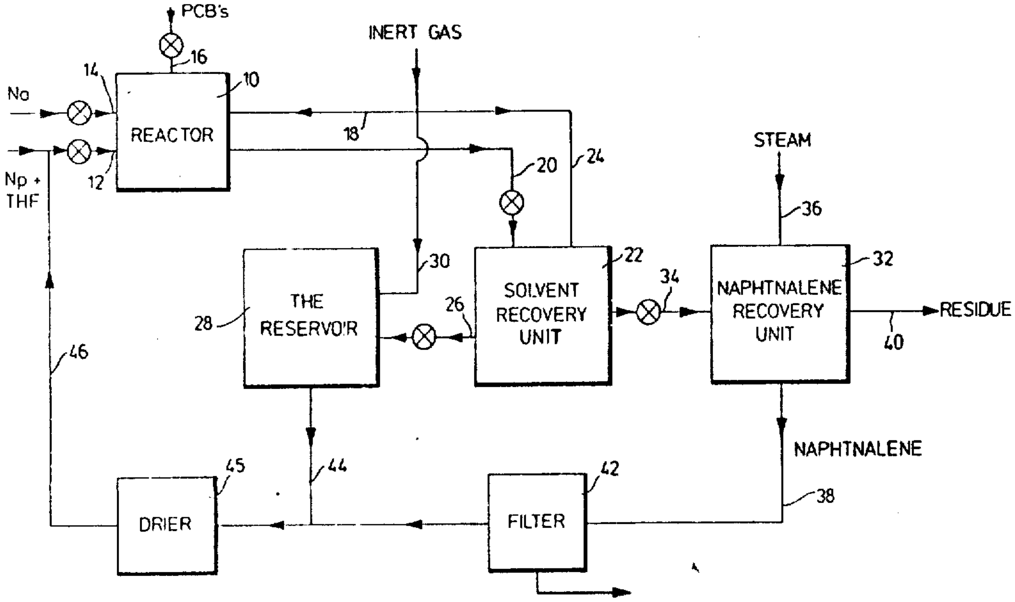

10 Claims, 1 Drawing Figure